United States Patent [19]
Seliger et al.

[11] Patent Number: 5,546,580
[45] Date of Patent: Aug. 13, 1996

[54] METHOD AND APPARATUS FOR COORDINATING CONCURRENT UPDATES TO A MEDICAL INFORMATION DATABASE

[75] Inventors: Robert Seliger, Winchester; Fred W. Ehrhardt, Lynnfield; Andrew S. Braunstein, Chestnut Hill, all of Mass.

[73] Assignee: Hewlett-Packard Company, Palo Alto, Calif.

[21] Appl. No.: 228,490

[22] Filed: Apr. 15, 1994

[51] Int. Cl.$^6$ .................................................. G06F 17/30
[52] U.S. Cl. .................................................. 395/600
[58] Field of Search ...................... 395/600, 425, 395/575; 364/413

[56] References Cited

U.S. PATENT DOCUMENTS

| | | | |
|---|---|---|---|
| 4,635,189 | 1/1987 | Kendall | 395/600 |
| 4,893,270 | 1/1990 | Beck et al. | 364/400 |
| 5,072,383 | 12/1991 | Brimm et al. | 364/413.02 |
| 5,361,202 | 11/1994 | Dove | 364/413.01 |

OTHER PUBLICATIONS

Korth & Silberschatz, Database System Concepts 2/e Mc-Graw-Hill, Inc., 1991.

T. A. Andrews et al, "Concurrency Control", Object Magazine, Jul.-Aug. 1993, pp. 39-43.

"HP CareVue 9000 Architecture Considerations", Hewlett-Packard Company Brochure, Sep. 1991, 4 pages.

"HP CareVue 9000 Clinical Information System", Hewlett-Packard Company Product Guide, Sep. 1993.

*Primary Examiner*—Thomas G. Black
*Assistant Examiner*—Peter Y. Wang

[57] ABSTRACT

A method for coordinating updates to a medical database in a medical information system permits concurrent charting from different workstations and medical instruments. A first data value for a record is entered at a first workstation and a second data value for the record is entered at a second workstation without locking either workstation during data entry. The new data values are stored in the medical database after completion of data entry at each workstation, and a correction history is recorded. The correction history contains information as to the update of the record with the first data value and the second data value. The record is updated with the first and second data values without aborting user activities or notifying a user that an update conflict has occurred. After the new data values are stored in the medical database, all workstations containing a copy of the record are updated to reflect the current state of the record.

18 Claims, 10 Drawing Sheets

METHOD AND APPARATUS FOR COORDINATING CONCURRENT UPDATES TO A MEDICAL INFORMATION DATABASE

FIELD OF THE INVENTION

This invention relates to medical information systems and to methods and apparatus for entering and changing information in a medical information database by a plurality of concurrent users.

BACKGROUND OF THE INVENTION

Large information systems utilizing a single database which is shared by a number of simultaneous independent users are becoming commonplace. In such systems, the users typically have the ability to add, delete and modify separate data entries, or records, in the centralized database and, therefore, it is imperative to control access by each individual user to each record so that two users do not modify the same record at the same time. If simultaneous access to records is not carefully controlled, a so-called "concurrent use" problem arises.

Specifically, in a typical database, database operations such as adding, modifying or deleting records are performed by the users at physically separate terminals which may be located remotely from each other. Each user enters information into the terminal to enable the database system to perform a requested operation, but generally the actual changes to the record are not made until the user has completed a requested change at the terminal and then initiated an update procedure by an additional operation (for example by selecting a "store" button on a graphic user interface). In some database systems, users may actually simultaneously request different changes to the same record at two different terminals.

However, the database software which actually makes the changes to the records performs the update operation in a serial fashion. If change requests to the same record are made simultaneously, special arbitration routines decide which request will be handled first. In such a system, if simultaneous access to records is allowed, a record may be modified by one user and then immediately changed by another user, resulting in erroneous or confusing results.

Consequently, most modern database systems utilize some type of record "locking" procedure which prevents simultaneous access to the same record. Typically, such systems require that a particular record be "read" before modification of the record is attempted. When a record is "read", the database system marks the record as "in use". Subsequently, if another user requests access to the "in use" record by attempting to read the record, a notification is sent to the second user indicating the record is not available because it is being modified by a prior user. This record locking scheme, sometimes referred to as the "pessimistic locking model", generally works well and prevents the confusion and errors which result from simultaneous access.

However, in some circumstances, the aforementioned record locking scheme can create problems, for example, in systems where each record contains a large amount of information. Inefficiency results due to the fact that an entire record must be locked even if only a small portion is being modified; therefore, a user who wishes to update a locked record must wait until the record is free, even if another user is modifying a completely different part of the record.

For example, the latter situation can occur in a hospital setting in which care providers enter information concerning patients into a medical information system. The information may include patient status information such as pulse rate, respiration and other such variables (measured over time) and may also include information such as medication administered and tests performed. Such a medical information system operates analogously to a well-known manual flowsheet system in which patient information, readings, notes and comments are added serially, row-by-row to a paper record, known as a flowsheet, which is kept at the patient's bed.

Typically, in a medical information system, information is entered into a database for each patient by a variety of users, including doctors, respiratory therapists, clinical laboratories, nurses, and bedside devices, which automatically generate patient information. Many of these users are mobile and may not be in the vicinity of a given patient when they desire to enter information for that patient. Consequently, care providers are generally allowed to update the medical database from a variety of computer terminals placed at separate physical locations.

Since the amount of information added to the flowsheet can be substantial and continuously grows, the system quickly becomes inefficient if the entire flowsheet is locked each time a care provider enters or modifies information. The inefficiency is especially unfortunate because, although possible, it is unlikely that two different care providers will actually be modifying the same area of the flowsheet due to the fact that many care providers are specialized. It is possible to lock only portions of the flowsheet, so that two care providers operating on different areas of the flowsheet can concurrently enter or modify information, but due to the interrelationship of many flowsheet areas, such partial locking schemes are complicated and cumbersome.

Therefore, to avoid inefficiency, it is desirable to allow two or more separate care providers to enter or modify (collectively referred to as "chart") data concurrently for a single patient, so that no user has to wait while other users chart information. With such a concurrent entry system, it is critical that the data entered be consistent and that all users be informed when changes to the data are made, so that potentially serious errors do not occur.

Another approach to accessing database records is referred to as the "optimistic locking model". The user proceeds with a transaction, such as the updating of a record, on the assumption that there is no conflict. When the user attempts to commit the transaction, such as by storing the new information, the database software determines if there was a conflict with another user. If a conflict is found, the transaction is aborted. This approach enables all users to proceed without waiting. However, the transaction may be aborted at the end. The optimistic approach is undesirable in a medical information system, since the user may be required to reenter the information for updating the record, thus wasting valuable time.

One recordkeeping feature that has been used in connection with updating records in medical information systems is a correction history. The correction history contains a record of each change to each parameter in the patient flowsheet. Each entry in the correction history indicates the value of a parameter that was corrected, the user that made the correction and the time of the correction. Thus, the hospital has a complete record of all changes to each patient flowsheet. The correction history is particularly important in a hospital environment, which often involves life and death situations and may require later analysis of events that occurred during the care of a particular patient.

SUMMARY OF THE INVENTION

The present invention provides methods and apparatus for coordinating updates to a record, such as a patient flowsheet, in a medical information system. The method comprises the steps of entering a first new data value for a record in a medical database at a first workstation and a second new data value for the record at a second workstation without locking the first workstation or the second workstation during data entry, storing the first new data value in the record in the medical database after completion of data entry at the first workstation and storing the second new data value in the record in the medical database after completion of data entry at the second workstation, and recording a correction history for that record. The new data values are stored in the medical database without aborting the user's activities. Any update conflict is transparent to the user. The correction history contains information as to the update of the record with the first new data value and information as to the update of the record with the second new data value.

The record in the database is locked for a very brief time to prevent access by the workstations only during the steps of storing the new data values in the medical database, thereby enabling concurrent data entry at the first and second workstations without locking.

Preferably, a database event is defined for each set of new data values stored by a user. The database events are placed in buffers corresponding to the workstations, and the workstations are notified of the database events. The database events are transferred from the buffers to the corresponding workstations when each of the workstations requests such transfer. Preferably, each workstation registers an interest in selected database event types. The workstations are notified of only the selected database event types for which an interest has been registered.

Each workstation is updated to reflect recent changes to the record in response to notification of a database event. Each workstation is also updated to reflect recent changes to the record in response to a store request by the user. In either case, the workstation obtains all database events from the corresponding buffer and processes the database events in sequence so that the workstation is updated in synchronism with new data values entered at other workstations. The display screen of the workstation is updated only when the information on the display screen is altered by the database events and only after all database events have been processed.

The correction history provides a permanent record of all changes to the patient flowsheet and can be displayed at a workstation in response to a request by a user. The correction history resolves any confusion resulting from concurrent charting of information by different users.

BRIEF DESCRIPTION OF THE DRAWINGS

For a better understanding of the present invention, reference is made to the accompanying drawings, which are incorporated herein by reference and in which.

DETAILED DESCRIPTION OF THE PREFERRED EMBODIMENT

Figure 1:
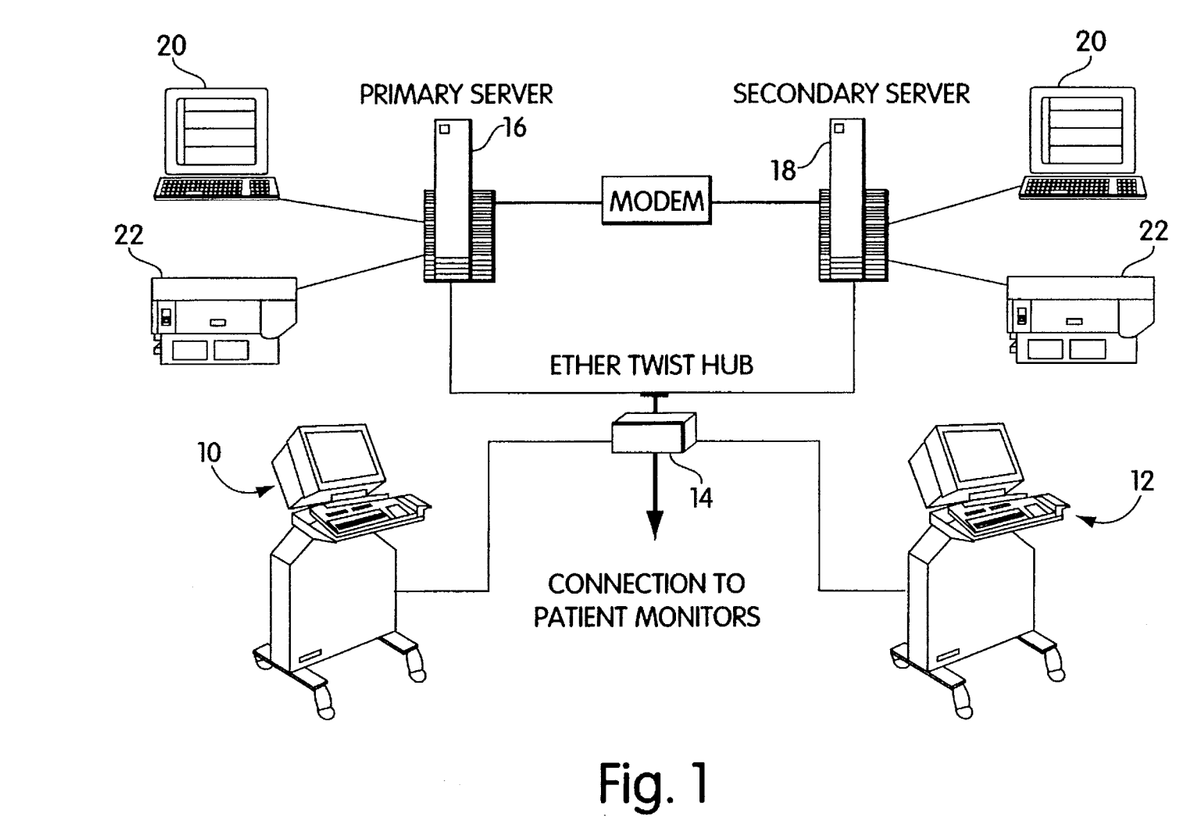
FIG. 1 is a schematic diagram of an illustrative medical information system which forms an operating environment for the invention.

The invention is preferably practiced in a medical information system, or clinical information system. The medical information system is designed to provide patient information at the patient's bedside in a hospital environment. An example of a basic medical information system is shown in FIG. 1. The system uses a client server architecture wherein a central server supplies data and controls the flow of information to workstations (clients) located at each patient bedside. The client server architecture eliminates the need for database storage at each workstation.

As shown in FIG. 1, workstations 10 and 12 are connected through a network hub 14 to redundant central servers 16 and 18. Each of the central servers 16 and 18 includes a central processor, memory and disk storage. The servers 16 and 18 perform centralized functions, such as database services, bedside device interface services, hospital system interface services and report services. Each central server typically includes a system manager terminal 20 and a printer 22. Workstations, only two of which are shown in FIG. 1, are typically located at patient bedsides and other locations as required throughout the hospital. Each workstation contains user interface programs and all application programs run by the workstation. The system may also be connected through hub 14 to patient monitors at selected patient bedsides. The patient monitors supply physiological information to the database. An example of a medical information system of the type shown and described is the HP CareVue 9000 System manufactured and sold by the Hewlett-Packard Company.

By way of example, workstations 10 and 12 can be HP 9000 workstations which operate with a diskless processor and include a high resolution graphic display, keyboard and trackball. The workstations typically include 16–32 megabytes of RAM. The central servers 16 and 18 can be implemented as HP 9000 processors coupled to 1.2 gigabytes of disk storage and including 24 megabytes of RAM. The system preferably uses the HP-UX operating system, a robust implementation of the AT&T Unix System V.2. The system also uses the X/Windows graphic user interface. The database is comprised of an HP-Allbase relational database and an object-oriented database shell. The system database is shadowed, meaning that it is maintained on both central servers 16 and 18. Both copies of the database are updated with each transaction. Data is initially stored at the workstation and is moved to the server to be stored in the medical database.

Figure 2:
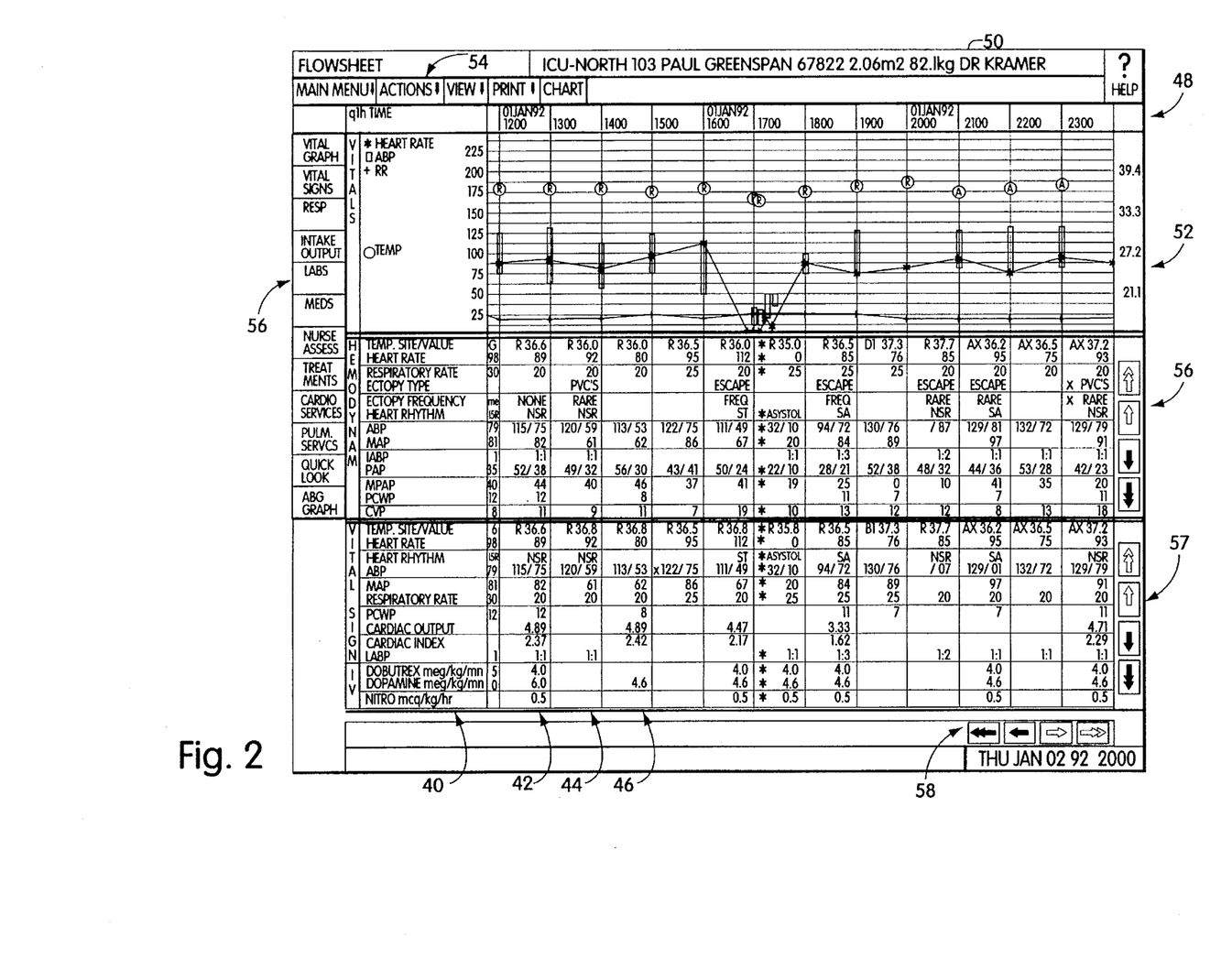
FIG. 2 is an example of a patient flowsheet display in the medical information system of FIG. 1.

An example of a patient flowsheet display as it may appear on one of the workstation display screens is shown in FIG. 2. The flowsheet provides a concise summary of selected patient information for a given time period. In the example of FIG. 2, various patient parameters 40 are listed in the left hand column of the flowsheet, and parameter values 42, 44, 46, etc. are displayed for selected time increments from left to right. The times 48 of the parameter values are indicated along the top row of the flowsheet. The patient is identified in an area 50 at the top of the screen, and graphic representations of selected parameters are displayed in an upper area 52 of the flowsheet. Menu selections 54 and 56 appear along the top and left sides of the flowsheet display. It will be understood that only a portion of the information contained in the patient flowsheet is displayed at any given time. Arrows 56, 57, 58 permit the flowsheet information to be scrolled up, down, left or right. A variety of different flowsheet formats can be utilized depending on the application. When menu selections are made, various windows appear on the display screen. For example, selection of "chart" permits charting of information into the flowsheet.

As noted previously, two or more users may attempt to chart flowsheet information for the same patient at the same time such as, for example, at workstations 10 and 12. Another possibility is that a user at a workstation may attempt to chart information on a patient flowsheet at the same time that the flowsheet is being automatically updated by an instrument, such as a patient monitor. Yet another possibility is that two instruments may attempt to update the same patient flowsheet at the same time.

In prior art systems, the patient flowsheet information in the database was read by one of the workstations or instruments, and all other workstations and instruments were locked out from the patient flowsheet during the data entry and update process. The lock could, in some cases, occur for an extended time period, but in any case was inconvenient and annoying to users that were locked out.

The present invention provides a method for concurrent charting, or updating, of records in a medical database without locking the record during data entry, without aborting user activities and without a requirement to notify the user in case of an update conflict. The invention is based on the recognition that concurrent updating without locking can be combined with the correction history to avoid delays in charting of medical information, without creating confusion or ambiguity in the stored medical information.

New information to be charted on a patient flowsheet is temporarily stored by the application program in the workstation performing the update. Thus, for example, a user may chart information for a patient flowsheet at workstation 10 (FIG. 1), and another user may chart information for the same patient flowsheet at workstation 12. The charting may be performed by the two users in the same or different parts of the flowsheet. When each user completes entry of the new information, he selects a "store" button on the graphic user interface using the trackball. At this time, the new information for updating the patient flowsheet in the database is transmitted from the workstation to the database in the central servers 16 and 18, and the database information is updated. During this brief time, the patient flowsheet in the database is locked, and other workstations cannot record data in the same patient flowsheet. However, since new information is stored locally in each workstation until the user has completed data entry and is ready for storing the information in the patient flowsheet, the data entry process is not interrupted or delayed.

In the event that two or more users attempt to store new information simultaneously, the central servers 16 and 18 handle the store requests in the order in which they are received. Even though the store requests may be made simultaneously by users at different workstations, the store requests will, in fact, be recognized serially by the computers in the central servers 16 and 18. Furthermore, users are unable to predict the order in which their store requests will be processed. The first store request is processed and the associated new information is entered into the patient flowsheet in the database. Then the second store request is processed and the new information for that request is entered into the patient flowsheet in the database. During the processing of each store request, the patient flowsheet in the database is locked. However, the lock period is very short, typically less than two seconds, whereas, in prior art systems, the patient flowsheet could be locked for an indefinite period during data entry. The store operation is described in more detail below.

Figure 3:
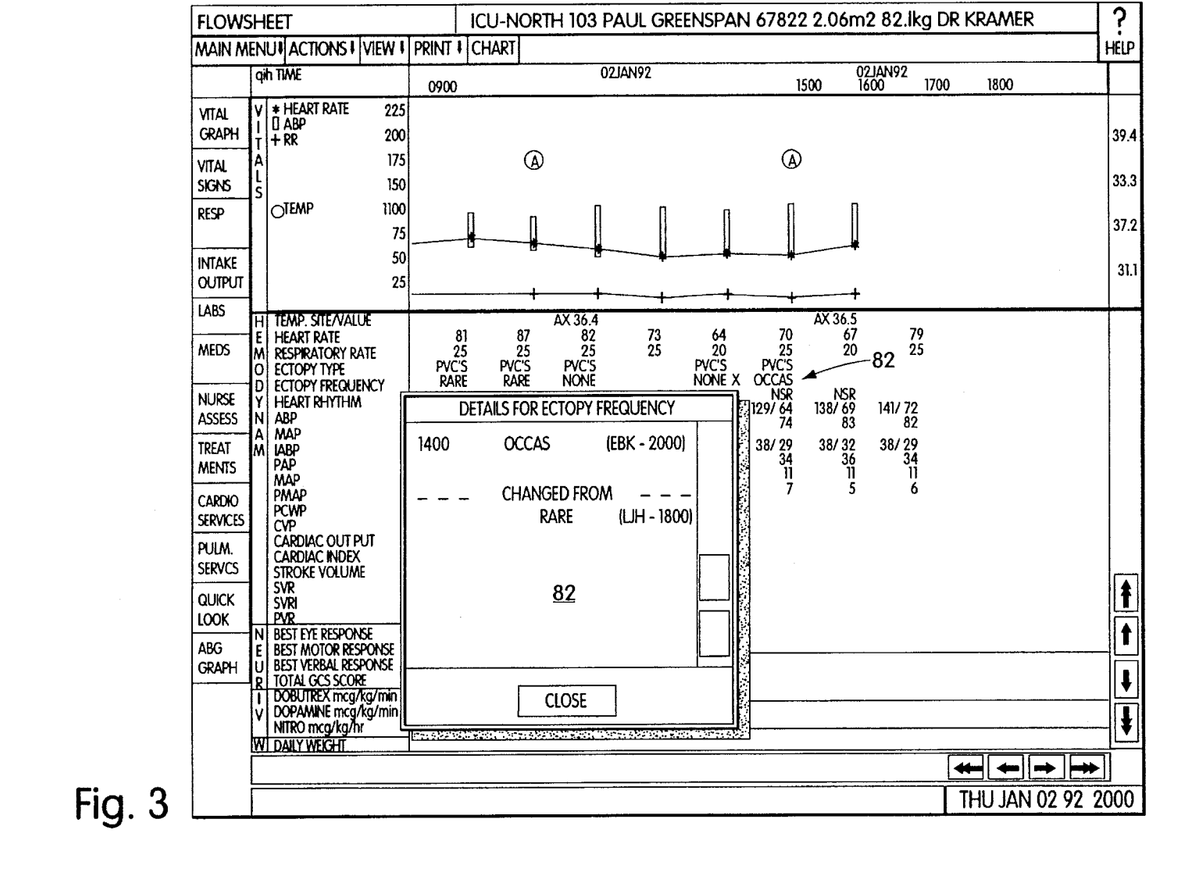
FIG. 3 is an example of a correction history superimposed on a patient flowsheet display in the medical information system of FIG. 1.

Since the patient flowsheet in the database is locked only during the brief period when new information is being stored in the database, the same parameter in the patient flowsheet may be updated concurrently by users at different workstations. Concurrent update of the same parameter could potentially cause confusion to system users. One of the users would observe a new parameter value on his display screen different from one he had just entered. Furthermore, the first new parameter value in the database would immediately be overwritten by the second new parameter value. The correction history eliminates any confusion. Each time the parameter value is changed, the correction history is updated for that parameter. The new parameter value, the user making the change and the time of the entry are added to the correction history, and the new parameter value becomes the current value. In the case where two users change the same parameter concurrently, the correction history would have two entries, one for the first update to be processed and one for the second update to be processed. The correction history for a newly-modified parameter can be selected by the user clicking on the newly-modified parameter on the display screen. The correction history is displayed as shown in FIG. 3 and informs the user of recent updates to that parameter. The correction history also provides a permanent record of changes to the patient flowsheet so that any discrepancies can be analyzed at a later time.

It may appear that concurrent updating of the same parameter in a patient flowsheet would be undesirable from a system operation viewpoint. However, this is not the case when concurrent updating is used with the correction history. In the medical information context, neither new entry has priority. For example, if one user enters a heart rate of 80 for a given patient and another user concurrently enters a heart rate of 90 for the same patient, the entries are clearly different. However, the system is not expected to determine which data entry is correct or to assign either data entry a priority. In effect, the system doesn't care which data entry is received first. All that is required is to record the data entries in the order in which they were received and to reflect all updates in the correction history. There is no requirement to abort either transaction or to inform one of the users that a conflict has occurred.

The current flowsheet information must be reflected in each workstation which contains a copy of the patient flowsheet that was updated. Each workstation is notified by the database server that an event has occurred for a particular patient flowsheet. Each workstation containing that patient flowsheet requests the updated information from the server when it is ready to do so. The display screen of each workstation presently displaying the patient flowsheet is updated to reflect the new parameter value or values. The new parameter values are highlighted with a special character, such as an "x" or "!". The update of flowsheet information in workstations is described in detail below.

As noted above, the user can select the correction history for the updated parameter value, and the correction history is superimposed on the flowsheet display. From the correction history, the user can determine the source of the update. Furthermore, in the case of concurrent updates to the same parameter, each user can determine exactly what happened. This is particularly useful for the user who updated the parameter value but observed that a different parameter value was entered into the flowsheet as a result of a concurrent entry by another user. In FIG. 3, a parameter value 80 for ectopy frequency at time 1400 is indicated by an "x" as having been updated. A correction history 82 indicates the recent changes to the modified parameter value.

Figure 4:
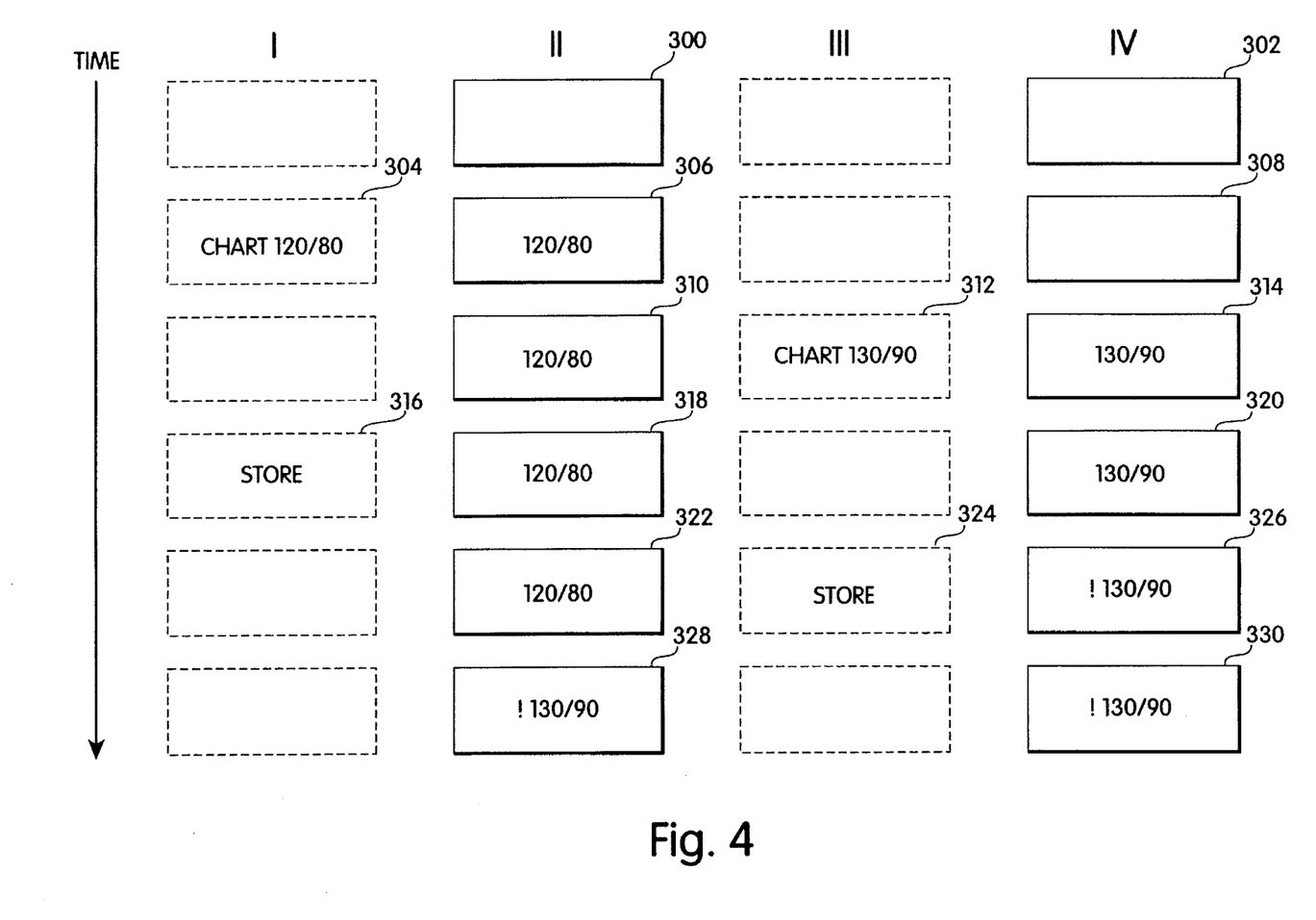
FIG. 4 is a schematic diagram illustrating the information displayed on two workstations over time as seen by two users who attempt to simultaneously chart the same flowsheet entries for a single patient in the medical information system.

FIG. 4 shows a schematic diagram of relevant portions of the workstation displays of two separate users (user "A" and user "B") who simultaneously attempt to make a flowsheet entry on the same flowsheet row at the same charting time. Each horizontal row in FIG. 4 represents an instant in time or a short time interval and illustrates each user's action (shown in dotted boxes) and the corresponding workstation display. In FIG. 4, time increases in a downward direction and the first column (I) illustrates user A's action, the second column (II) indicates user A's workstation display, the third column (III) illustrates user B's actions and the fourth column (IV) indicates user B's workstation display.

More particularly, boxes 300 and 302 indicate an instant of time during the initial state of the database system in which neither user has acted and both displays are blank. During the next instant of time, as represented by boxes 304, 306 and 308, user A enters a particular value, for example, a blood pressure reading of 120/80 for a patient into his workstation as shown in dotted box 304. As illustrated in box 306, while user A enters the new information, the entered value is displayed on his workstation display to provide feedback and to allow editing before the actual data storage is performed.

As described above, the database server does not actually begin a data storage procedure until user A instructs the database server to store the information by selecting the "store" button on the graphic user interface. During the data storage procedure, the entered value is first transmitted from the workstation to the database server where the physical storage mechanism is located and then stored in the appropriate database file. After the storage is complete, all displays which reference the stored value are updated to reflect the new stored value. Consequently, user B's display (as shown in box 308) does not display the value being entered by user A during the time instant represented by boxes 304, 306 and 308.

In the illustrated transaction, in the next instant of time, as shown by dotted box 312, user B enters a new value of blood pressure (for example, 130/90) after user A has entered the previous 120/80 value but before user A has instructed the database system to store the entered value. Thus, as shown by box 314 in column IV, the new value entered by user B is initially displayed on user B's workstation display. Since the new value entered by user B has not been stored at this time (user B has not initiated a STORE operation), the display on user A's workstation still indicates the value originally entered by user A, as illustrated in box 310.

During the next instant of time (as represented by boxes 316, 318 and 320) user A issues a command shown in dotted box 316 to the database server to store the blood pressure information entered in box 304 in the patient's flowsheet. In accordance with the operation of the inventive correction history system, it should be noted that the information shown on user B's display as illustrated in box 320 does not change, since B's display is not updated at this time. However, the database system generates a correction history. Thus, during the next instant of time (as represented by boxes 322, 324 and 326) when user B issues a store command to the database server, user B's display shows a special character (in this case an exclamation point) which indicates that the value shown on B's display (130/90) is a correction of a previous entry made by another user, in this case A. Finally, during the next instant of time (as represented by boxes 328 and 330), user A's display is updated to the current value of 130/90, indicating that a change has been made to that value entered by another user, and the exclamation point identifier is also displayed on A's workstation.

Figure 5:
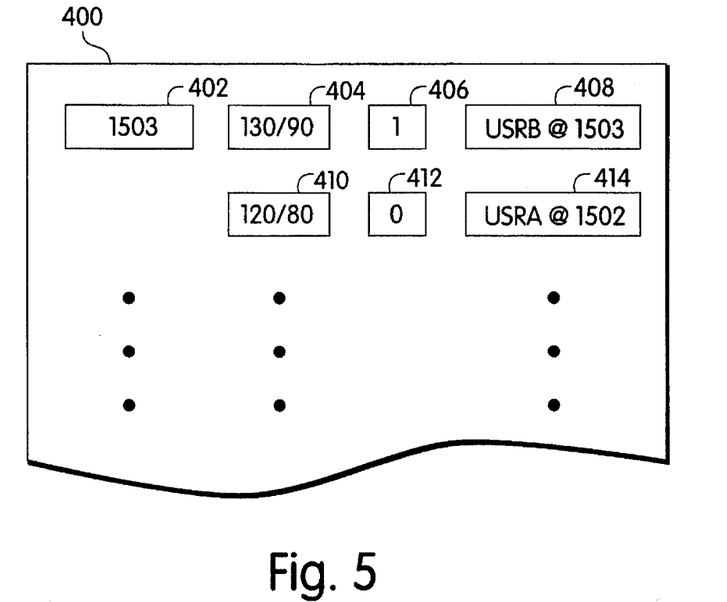
FIG. 5 schematically illustrates the details of a correction history file generated by the transactions illustrated in FIG. 4.

The correction history which is created by the system in the transactions illustrated in FIG. 4 is shown in FIG. 5. In FIG. 5, the correction history 400 consists of several storage locations for storing various information entries comprising a correction history for a particular point in time for a given parameter value in the flowsheet. For example, the correction history illustrated in FIG. 5 corresponds to field value for blood pressure at time 15:03 (24-hour time is used to avoid ambiguities). The time corresponding to the correction history entry is illustratively included in a box 402 at the left hand side of FIG. 5. The lowest line in the correction history, consisting of boxes 410, 412 and 414 indicates the original entry of the blood pressure value of 120/80 (shown in box 410) as entered by user A at time 15:02, as shown in box 414. Also included in the correction history is a flag value 412 which is initially set to a value of "zero" indicating that this is not a corrected value. The subsequent entry of the value 130/90 by user B previously discussed in connection with FIG. 4 is illustrated by the top row of FIG. 5, consisting of boxes 402, 404, 406 and 408.

As shown in the top correction row, the new blood pressure value 130/90 in box 404 is entered by user B, as indicated by box 408, which indicates that user B entered the new value at time 15:03. In addition, the flag in box 406 has now been set to a value of "one" to indicate that the new value is a corrected value. This flag causes an indicator to be displayed on each workstation with the affected parameter to indicate that the value has been corrected. In the illustrative embodiment shown, an exclamation point (!) is used, but any other character could be used in its place or, alternatively, changes in color or intensity of the displayed characters could be used. A user seeing the exclamation point then can refer to the correction history shown in FIG. 5, which is superimposed over the flowsheet as shown in FIG. 3, to determine that the value initially entered by user A was subsequently changed by user B to a new value. The correction history file gives a consistent indication of the changes made to each value so that mistakes can be avoided in interpreting values on the screen.

Although the transactions indicated in FIGS. 4 and 5 are possible, they are discussed more for illustration purposes and would be unusual because it is unlikely that two users would chart different values for the same flowsheet parameter at the same or nearly the same time. On the other hand, "collisions" will more likely occur where two users enter different data for different flowsheet values where the data are used in the calculation of another value. This can happen in several cases, including transactions that involve physiological calculations. In transactions of this type, the calculated value must already have been stored in order for the collision to generate a correction history.

Such collisions occur because the calculations can take place in several different physically remote areas. For example, a calculation of oxygen consumption (VO2) depends in part on a hemoglobin reading (Hgb) and a cardiac output data entry (CO). The oxygen consumption calculation can be made at either a clinical laboratory interface (CLI) or at a workstation, depending on the timing and data entry of the different parameters.

Figure 6:
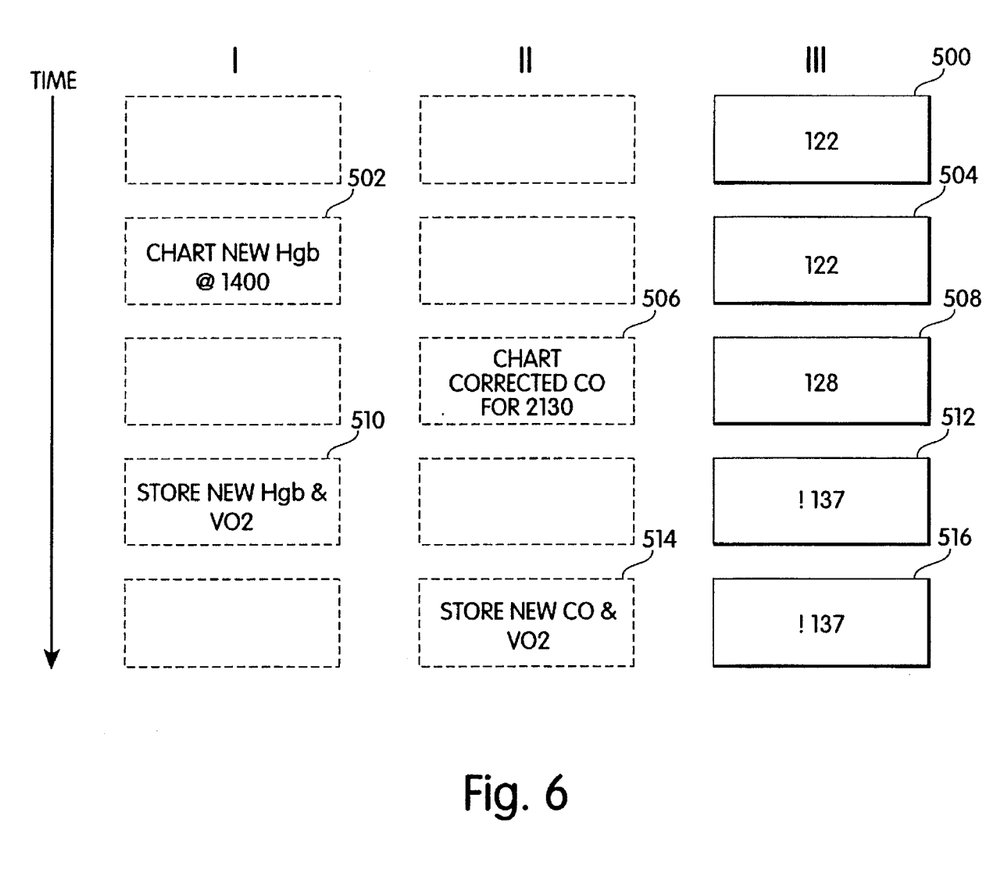
FIG. 6 is a schematic diagram illustrating the information displayed on a workstation over time as seen by a user where the user enters data into the system and a clinical laboratory interface also enters data which affects the data entered by the user.

FIG. 6 illustrates the display of oxygen consumption on a user's workstation and the changes which are a result of new values being entered substantially simultaneously entered by the clinical lab interface and a user. In particular, column I of FIG. 6 indicates the actions taken by the clinical lab interface; column II illustrates the actions taken by a user "B" and column III shows the display on user B's workstation of the oxygen consumption value.

As shown in the first line of FIG. 6, consisting of box 500, a value of "122" for the computed oxygen consumption is initially shown on user B's workstation display. This this value may be the result of previous calculations and previously-entered values for hemoglobin and cardiac output. Illustratively, the value 122 is assumed to be calculated from a hemoglobin reading taken at 07:00 and a cardiac output reading taken at 21:30.

In the second line of FIG. 6, represented by boxes 502 and 504, a new value of the hemoglobin reading (Hgb) taken at time 14:00 is charted by the clinical lab interface (note that the time the reading is taken can differ from the time at which the value is charted). Since the new time (14:00) for the hemoglobin reading is closer in time to the original time of 21:30 at which time the cardiac output was last entered, the new hemoglobin reading replaces the original hemoglobin reading taken at 07:00 and causes a new calculation of the oxygen consumption at the clinical lab interface resulting in a new value of 125.

However, as shown in box 504, this new oxygen consumption value is not reflected in the display at user B's workstation because the new hemoglobin value charted at the clinical lab interface has not yet been stored.

Assuming, in the meantime, that user B enters a corrected cardiac output value taken at time 21:30, this new cardiac output value causes a new calculation of the oxygen consumption at B's display, which is shown in box 508, and results in a new value of 128, which is displayed at user B's terminal.

Subsequently, as shown in the row represented by boxes 510 and 512, the clinical lab interface stores the new hemoglobin reading and oxygen consumption value computed by it as shown in box 510. In response to a new value of the hemoglobin reading, the computer system updates the display at user B's workstation (as indicated in box 512) reflecting both the new cardiac output value entered by user B and the new hemoglobin value charted by the CLI. An exclamation point is displayed because the CLI has just corrected the oxygen consumption value based on the new hemoglobin reading.

Alternatively, the new hemoglobin reading causes a recalculation of the oxygen consumption at user B's workstation which is then displayed on the workstation as shown in box 512.

Subsequently, in the line represented by boxes 514 and 516, user B stores the new cardiac output and oxygen consumption values as shown in box 514. However, (as shown in box 516) the display at user B's workstation does not change because it is already consistent with the new input values.

Figure 7:
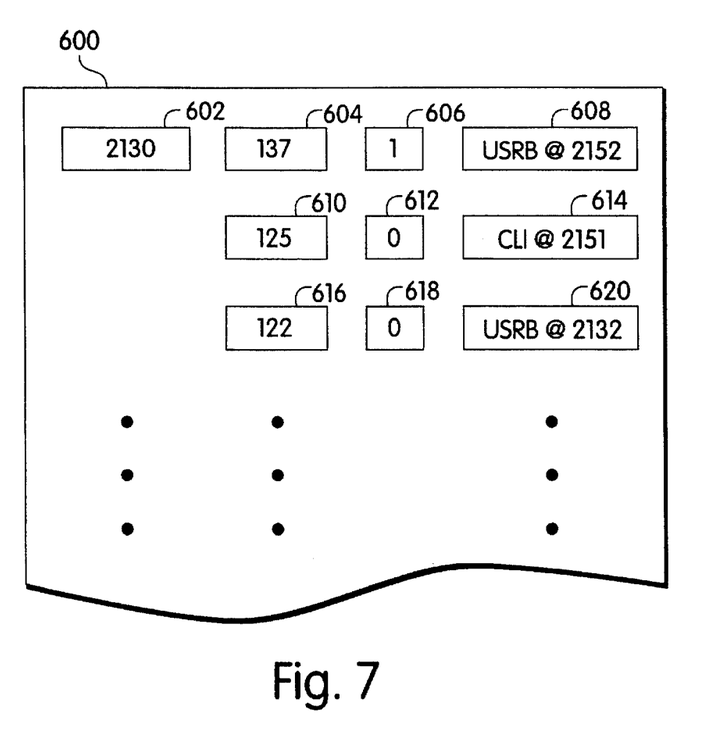
FIG. 7 schematically illustrates the details of a correction history file generated by the transactions illustrated in FIG. 6.

At this point, there will be two corrections to the oxygen consumption value, one due to the more recent hemoglobin reading and the second one due to the new cardiac output reading; after user B stores the new cardiac output value and the computed oxygen consumption values, the correction history details for the oxygen consumption at time 21:30 will be as shown in FIG. 7.

As in the correction history previously described in connection with FIG. 5, the time of the correction history is indicated in box 602 as 21:30. This time is indicated as the time at which the correction applies and is not the time at which the corrections were actually entered. The correction entry times are shown in the body of the table as hereinafter discussed. As shown in the lowest row of FIG. 7, illustrated by boxes 616, 618 and 620, the oxygen consumption value of 122 originally displayed on user B's display was caused by an entry shown in box 620 by user B at time 21:32 resulting from the cardiac output reading at time 21:30. At this time (as shown in box 618), the change flag is set to "zero" indicating that this is not a changed value.

The next row, represented by boxes 610, 612 and 614, indicates the change in the oxygen consumption value caused by the charting of the new hemoglobin reading taken at time 14:00 and entered at time 21:51 by the clinical lab interface. As indicated by box 614, this causes a new computation of the oxygen consumption resulting in a value of 125 (indicated in box 610). It should be noted that the value of 125 is not displayed on user B's workstation because, prior to the time that the new hemoglobin value was stored, user B entered a new cardiac output value. Consequently, the change flag 612 still remains at "zero" at this point.

Finally, the uppermost row, consisting of boxes 604, 606 and 608, represents the change to the value displayed on user B's workstation caused by the new entry of the cardiac output occurring at time 21:52. As shown in box 608, this new value, in turn, results in a new value of the oxygen consumption of "137" as shown in box 604. In addition, since this new value corrects the value of 125 calculated by the clinical lab interface (shown in box 610), the change flag illustrated by box 606 is now set to a value of "one". The change flag causes an exclamation point to be displayed on all workstations, which alerts the users to examine the correction history to determine what happened during the entry of the new values.

Figure 8:
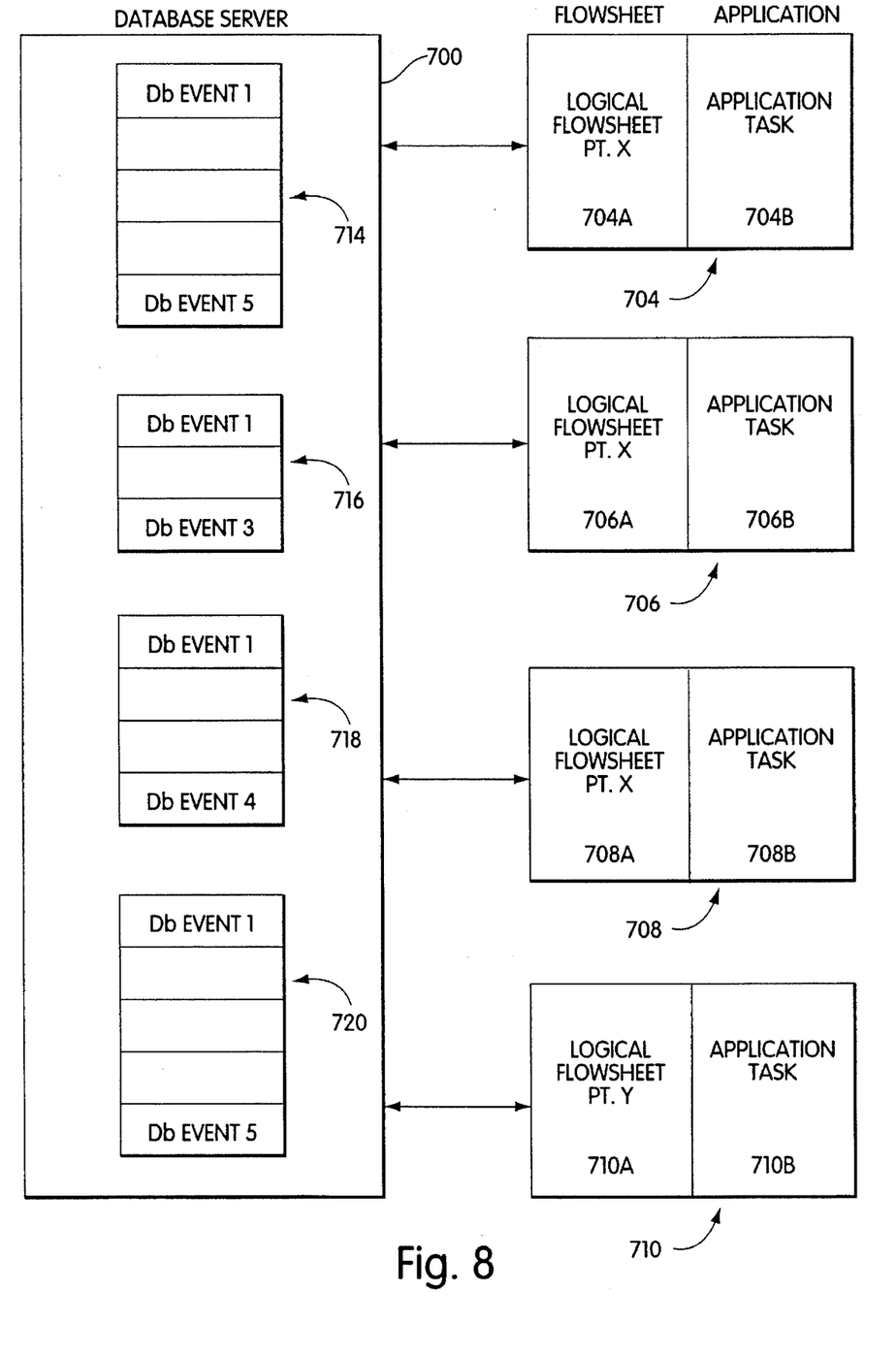
FIG. 8 is a simplified schematic diagram of those software components of the medical information system which are relevant to concurrent charting.

A simplified schematic diagram of those components of the system software that are relevant to concurrent charting of patient information is shown in FIG. 8. A database server 700 located in each of the central servers 16 and 18 (FIG. 1) performs updating of the medical database in disk storage and remote update of flowsheet information in the workstations. Flowsheet applications 704, 706, 708 and 710, four of which are illustrated in FIG. 8, communicate with the database server 700. A flowsheet application resides in each workstation in the hospital. Each flowsheet application includes a logical flowsheet and an application task. For example, flowsheet application 704 contains logical flowsheet 704A for patient X and application task 704B. The logical flowsheet is a software representation of the flowsheet for a particular patient and, except for brief periods prior to completion of remote updating, is a copy of the patient flowsheet that resides in disk storage. The application task controls the graphic user interface and the display screen of the workstation. For example, the user may select different flowsheet information from the information that is presently being displayed or may chart new information on the flowsheet. In the example of FIG. 8, flowsheet applications 704, 706 and 708 contain the logical flowsheet for patient X, and flowsheet application 710 contains the logical flowsheet for patient Y. Each workstation may contain more than one flowsheet application, since the workstations may accommodate multiple users. The database server 700 contains buffers 714, 716, 718 and 720. As described below, the buffers 714, 716, 718 and 720 are queues of events for updating logical flowsheets 704A, 706A, 708A and 710A, respectively.

Figure 9:
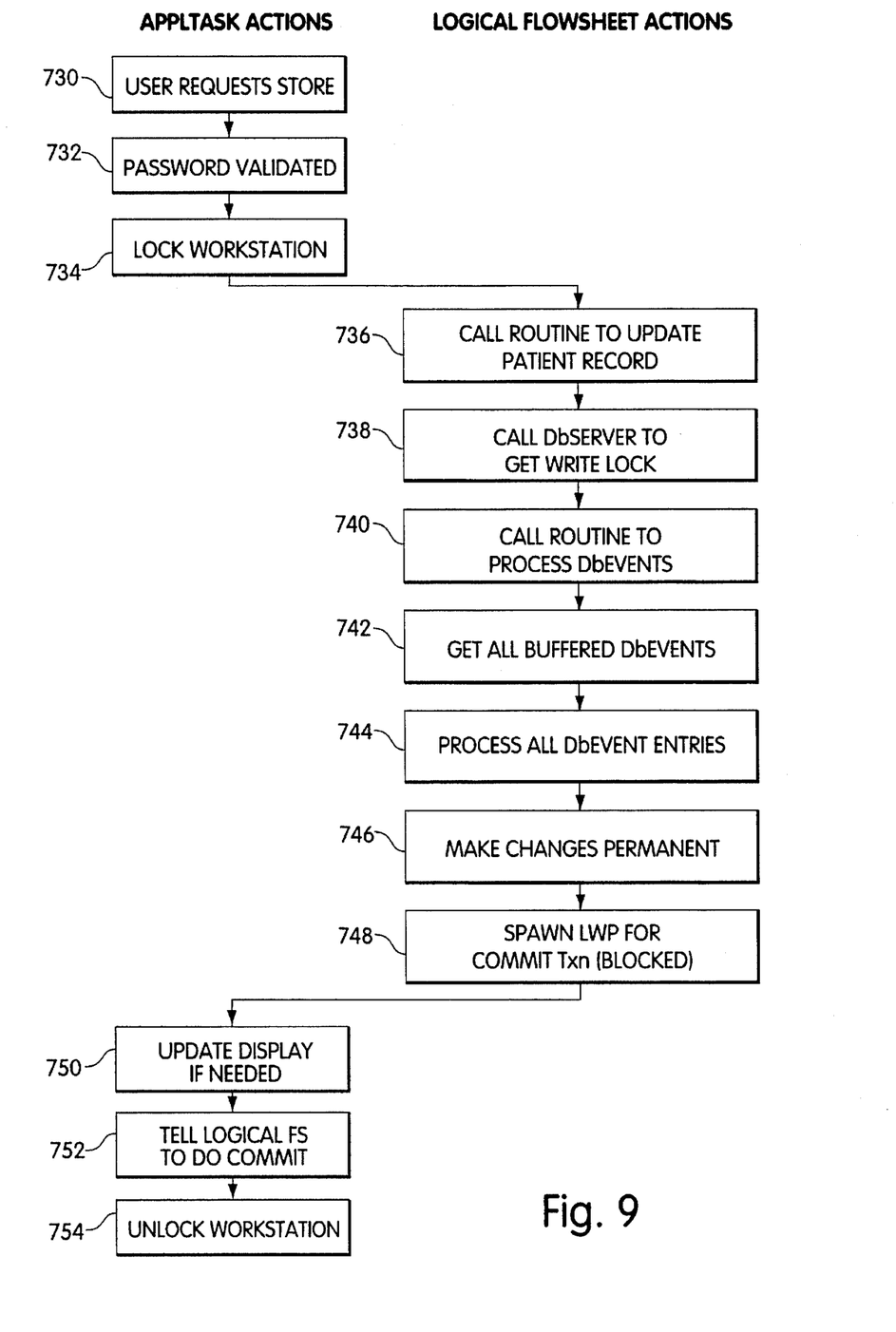
FIG. 9 is a flow diagram of the store operations by the flowsheet application.

The store operations for each flowsheet application are illustrated in FIG. 9. Operations by the application task are shown on the left side of FIG. 9, and operations by the logical flowsheet are shown on the right side of FIG. 9. As noted previously, data entered by a user for updating the flowsheet is temporarily held in the workstation without locking the database record. When the user is satisfied with the new data, the user requests a store operation in step 730 by selecting the "store" button on the menu of the graphic user interface. At this time, a dialog box appears on the display screen and requests entry of a password by the user. If the password is validated in step 732, the workstation is locked in step 734. Locking of the workstation prevents further user operations and display updates until the store operation is completed. The workstation lock in step 734 locks only the workstation that is storing data in the flowsheet. The workstation lock is to be distinguished from the write lock of the database record, as described below. Next, a routine to update the patient record is called by the logical flowsheet in step 736. Then the logical flowsheet calls the database server to request a write lock for the patient record in the database. The write lock prevents all workstations and instruments from accessing the patient record in the database. In step 740, the logical flowsheet calls a routine to process database events, and in step 742 all buffered database events for the particular patient flowsheet are obtained from the database server 700.

The database events for each patient flowsheet are stored in buffers, or queues, on a per workstation basis in the database server 700. For example, buffer 714 (FIG. 8) contains database events for logical flowsheet 704A. Each database event includes a sequence number and event information. Database events typically represent new information, or data, for updating the patient flowsheet. The sequence represents the order in which the events were received by the database server, and the event information contains the new data for updating the flowsheet. The buffer may contain multiple database events because of recent or concurrent entries from other workstations or instruments.

By obtaining all buffered database events in step 742, the flowsheet application synchronizes the locally-generated change with any other changes to the flowsheet since the last update performed by that flowsheet application. This permits concurrent entries to be processed in the order in which they are received by the database server.

In step 744, all database events obtained from the buffer are processed in the order of their sequence numbers, and the changes are made permanent in step 746. The processing of each database event involves updating the appropriate parameter values in the logical flowsheet and determining if the update requires the display screen to be updated. However, the display screen is not updated until all database events have been processed. As noted previously, only a portion of the flowsheet information for a given patient is displayed at any given time. Processing of the database events also involves recording a correction history for each parameter that is changed. The new parameter value is added to the correction history, and the new value becomes the current value in the logical flowsheet. Each entry in the correction history includes a parameter value, the user's ID and the actual charting time of the parameter value. To avoid multiple entries of the same correction, the correction history is updated for only those events that originated at the logical flowsheet performing the store operation. As a result of processing two or more database events in sequence, the same parameter value may be changed more than once. By adhering to the sequence numbers of the database events, the final parameter value reflects the current value. In the case of concurrent charting, database events are processed in the order received by the database server.

In step 750, the workstation display is updated if necessary. Although the processing of database events may result in multiple changes to the flowsheet information, the display screen is updated only after all database events have been processed and only if the information currently being displayed has been changed. The processing of all database events in step 744 prior to updating the display in 750 avoids the situation where the display screen is updated several times in rapid succession to reflect concurrent or nearly concurrent changes by different users and/or instruments.

In step 752, the flowsheet application requests the database server to commit the changes to the patient's record in the database and to unlock the patient's record in the database. The patient record is now available for further updating by other workstations or instruments. Typically, the write lock time between steps 738 and 752 is on the order of about two seconds. Even during the time that the patient record is locked, the user can chart new information in the flowsheet. The write lock would be noticed only briefly during an attempt to store new information in the patient flowsheet. In step 754, the workstation is unlocked, thus permitting further user interaction.

Figure 10:
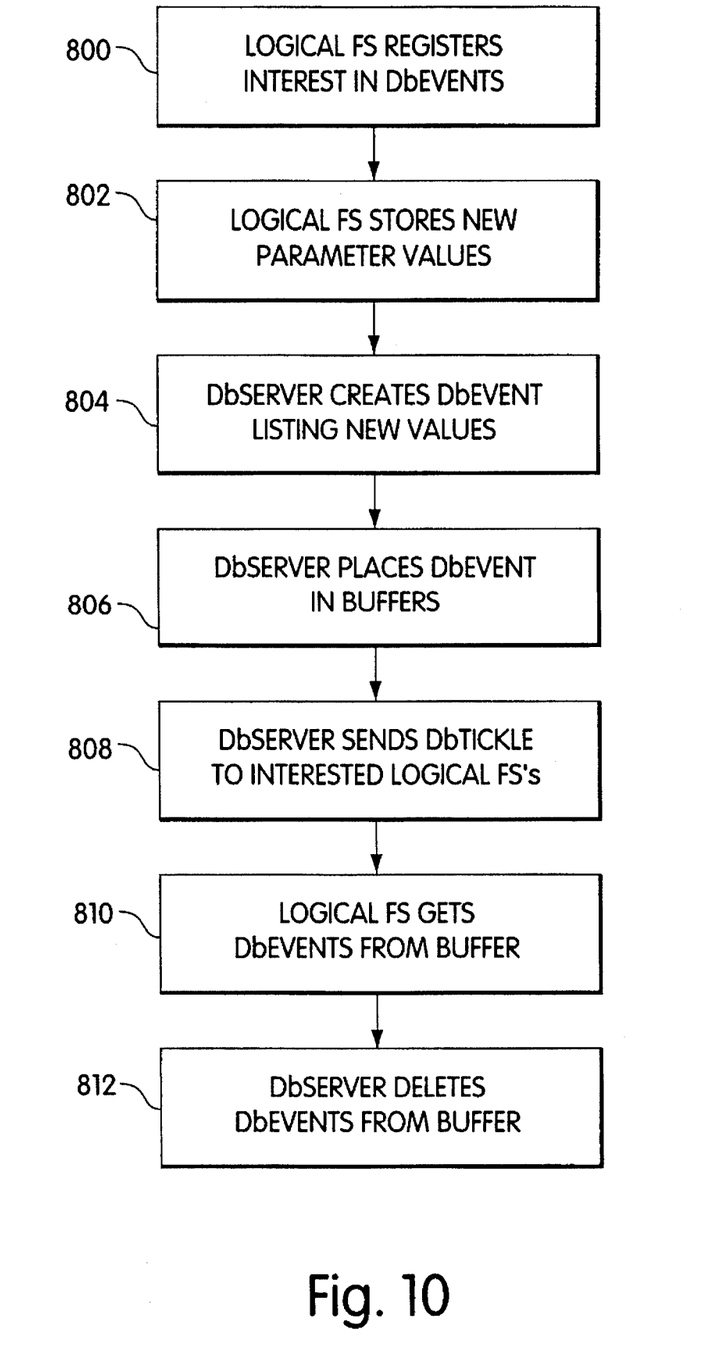
FIG. 10 is a flow diagram of the store and remote update operations by the database server.

The functions of the database server during the store operation and the remote update operation are shown in FIG. 10. As a part of the initialization of a workstation session with a patient flowsheet, the logical flowsheet in the workstation in step 800 registers an interest in certain types of database events for that patient flowsheet. For example, the logical flowsheet may be interested in new parameter values, but not in narrative notes entered by other users. Typically, the patient flowsheet contains only essential medical information, such as vital signs, whereas the complete record for the patient includes additional nonessential information that is not required for the flowsheet. The database events of interest for each logical flowsheet are stored by the database server and are used later by the database server during remote updating of the logical flowsheets in each workstation.

In step 802, a logical flowsheet in one of the workstations stores a new set of parameter values for a particular patient record. As illustrated in FIG. 9 and described above, the database server stores the new parameter values in the patient record. In addition, the database server in step 804 creates a database event that lists the changes to the patient flowsheet. In step 806, the database server places the database event in the buffers of all flowsheet applications which have registered an interest in such database events. For example, with reference to FIG. 8, assume that logical flowsheet 704A stores a new parameter value for patient X. The database server 700, in addition to storing the new parameter value, creates a database event that lists the new parameter value and places the database event in buffers 716 and 718 for logical flowsheets 706A and 708A, respectively, because logical flowsheets 706A and 708A pertain to patient X. The database event is not placed in buffer 714 because logical flowsheet 704A originated the new parameter value and has already processed it. The database event is not placed in buffer 720 because corresponding logical flowsheet 710A pertains to patient Y. It is assumed that logical flowsheets 706A and 708A have previously registered an interest in the new parameter value.

In step 808, the database sends a database tickle to the logical flowsheets which have registered an interest in the new parameter value. The database tickle is a brief message that indicates to the logical flowsheet that its buffer contains a new database event for processing. The database tickle contains a sequence number, which indicates the chronological order of the database event and text, which may indicate the user that generated the database event.

Figure 11:
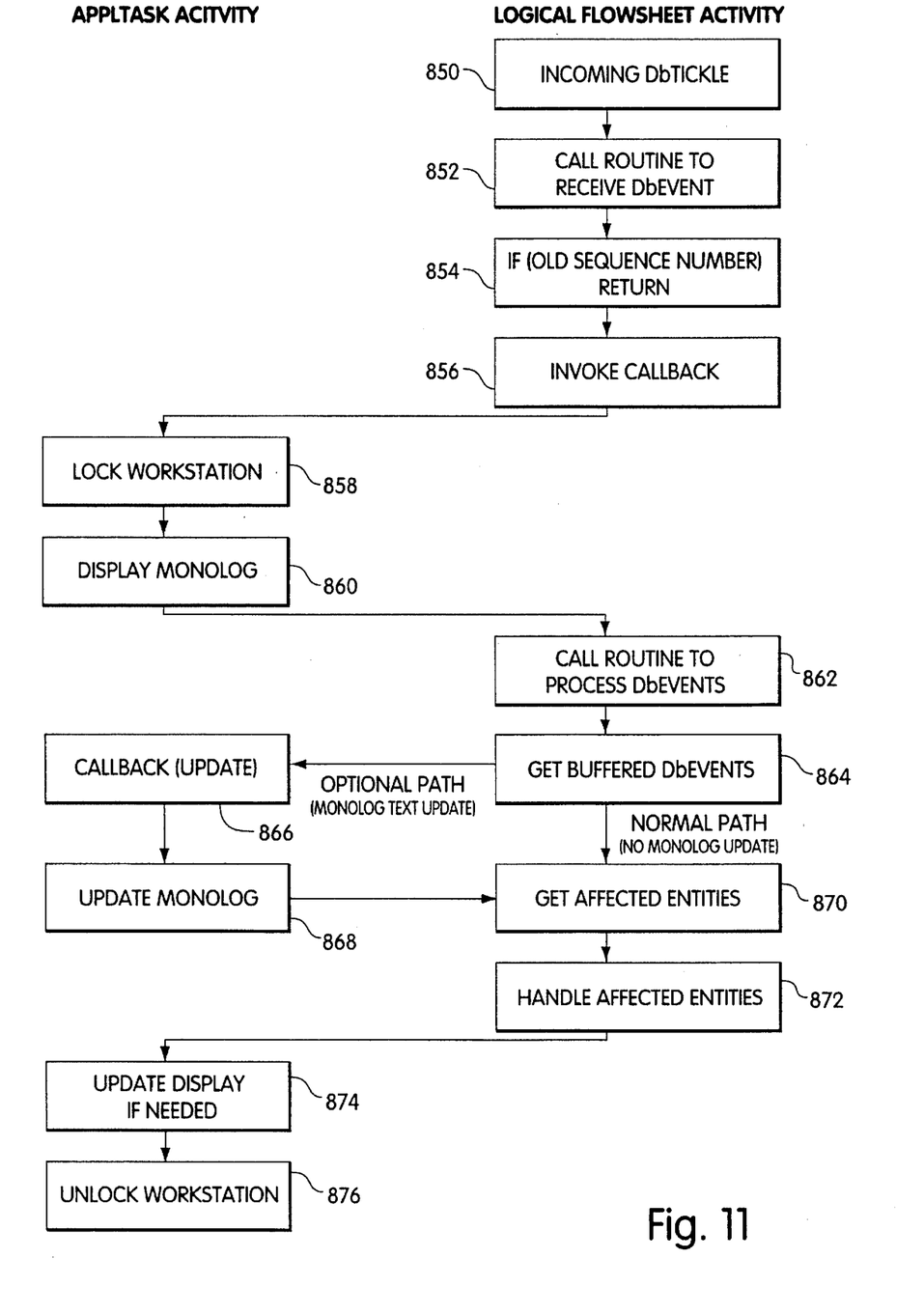
FIG. 11 is a flow diagram of the remote update operations by the flowsheet application.

The logical flowsheet in step 810 gets the database events, either immediately or at a later time when it is available to do so. The logical flowsheet may get the database events as part of a store operation, as shown in FIG. 9 and described above, or as part of a remote update operation, as shown in FIG. 11 and described below. After the logical flowsheet gets the database events, the database server deletes the database events from the buffer in step 812.

The remote update operations for each flowsheet application are shown in FIG. 11. Operations by the application task are shown on the left side of FIG. 11, and operations by the logical flowsheet are shown on the right side of FIG. 11. In step 850, the logical flowsheet receives the database tickle from the database server, indicating the presence of a database event in the buffer for that logical flowsheet. In step 852, the logical flowsheet calls a routine to receive database events. The sequence number of the database tickle is checked in step 854. If the sequence number identifies a database event that has already been processed by the logical flowsheet during a store operation, no update is required and the operation is terminated.

Assuming that the database tickle contains a new sequence number, a callback to the graphic user interface is evoked in step 856. The workstation is locked in step 858 so as to prevent further user interaction during the update process. In step 860, a monolog box is displayed. The monolog box indicates that the flowsheet is being updated as a result of a change by another user or instrument. For example, the monolog box may state "Data for this patient has been updated by (list of users). The flowsheet will be refreshed to retrieve this data".

In step 862, the logical flowsheet calls the routine to process database events and obtains all buffered database events from its corresponding buffer in step 864. If the buffer contains database events in addition to the one identified by the database tickle, a callback is evoked in step 866, and the monolog box is updated in step 868 to reflect the additional users or instruments that have changed the patient flowsheet. Steps 866 and 868 are omitted when the buffer does not contain additional database events.

In steps 870 and 872, the database events are processed as described above in connection with steps 744 to 748 in FIG. 9. That is, the database events are processed in sequence, and a determination is made as to the necessity for updating the display screen. The display screen is updated if necessary in step 874 after processing all database events, and the workstation is unlocked in step 876.

While the invention is described in terms of preferred embodiments in a specific system environment, those skilled in the art will recognize that the invention can be practiced, with modification, in other and different hardware and software environments within the spirit and scope of the appended claims.

What is claimed is:

1. A method for coordinating updates to a medical database in a medical information system, the method comprising the steps of:

entering a first data value for a record in said medical database at a first workstation and a second data value for said record at a second workstation, each of the workstations including a display screen;

permitting said first workstation to access said record in said medical database during data entry into said record at said second workstation and permitting said second workstation to access said record in said medical database during data entry into said record at said first workstation;

storing said first data value in said record in said medical database after completion of data entry for said record at said first workstation and storing said second data value in said record in said medical database after completion of data entry for said record at said second workstation, said first and second data values being stored in said medical database in dependent of the order in which they are entered at said first and second workstations; and recording a correction history for said record, said correction history containing information as to the update of said record with said first data value and information as to the update of said record with said second data value.

2. A method as defined in claim 1 further including the step of locking said record to prevent access to said record by said workstations only during the steps of storing said first and second data values in said record in said medical database, thereby enabling concurrent data entry at said first and second workstations.

3. A method as defined in claim 1 further including the steps of defining database events including a database event for each of said first and second data values, placing database event data representative of said database events in buffers corresponding to said workstations, notifying said workstations of said database events, and transferring said database event data from said buffers to the corresponding workstations when each of said workstations requests such transfer.

4. A method as defined in claim 3 further including each of said workstations registering an interest in selected database event types, wherein the step of notifying said workstations includes notifying each of said workstations of only the selected database event types for which an interest has been registered.

5. A method as defined in claim 3 wherein the steps of storing said first data value and storing said second data value include each of said workstations obtaining any database event data from a corresponding buffer, and processing said database event data in sequence so that each of said workstations is updated in synchronism with new data values entered at other workstations.

6. A method as defined in claim 5 further including the step of updating the display screen of each of said workstations only when information on said display screen is altered by said database events and only after all database event data has been processed.

7. A method as defined in claim 3 further including the step of updating a copy of said record in each of said workstations in response to notification of a database event, including obtaining any database event data from a corresponding buffer, and processing said database event data in sequence so that each of said workstations is updated in synchronism with new data values entered at other workstations.

8. A method as defined in claim 7 further including the step of updating the display screen of each of said workstations only when the information on the display screen is altered by said database events and only after all database event data has been processed.

9. A method as defined in claim 1 further including the step of displaying said correction history at each of the workstations in response to a request by a user.

10. A medical information system comprising:
- a central processor including a medical database, a first workstation for entering data into said medical database and a second workstation for entering data into said medical database, each of the workstations including a display screen;
- means for entering a first new data value for a record in said medical database at said first workstation and a second new data value for said record at said second workstation;
- means for permitting said first workstation to access said record in said medical database during data entry into said record at said second workstation and for permitting said second workstation to access said record in said medical database during data entry into said record at said first workstation;
- means for storing said first new data value in said record in said medical database after completion of data entry for said record at said first workstation and for storing said second new data value in said record in said medical database after completion of data entry for said record at said second workstation, said first and second new data values being stored in said medical database independent of the order in which they are entered at said first and second workstations; and
- means for recording a correction history for said record, said correction history containing information as to the update of said record with said first new data value and information as to the update of said record with said second new data value.

11. A medical information system as defined in claim 10 further including means for locking said record to prevent access to said record by said workstations only during the storing of said first and second new data values in said record in said medical database, thereby enabling concurrent data entry at said first workstation and said second workstation.

12. A medical information system as defined in claim 10 further including means for defining database events including a database event for each of said first and second data values, means for placing database event data representative of said database events in buffers corresponding to said workstations, means for notifying said workstations of said database events, and means for transferring said database event data from said buffers to the corresponding workstations when each of said workstations requests such transfer.

13. A medical information system as defined in claim 12 wherein each of said workstations further include means for registering an interest in selected database event types, wherein said means for notifying includes means for notifying each of said workstations of only the selected database event types for which an interest has been registered.

14. A medical information system as defined in claim 12 wherein said means for storing said first new data value and for storing said second new data value includes means for obtaining any database events from a corresponding buffer and means for processing said database event data in sequence so that each of said workstations is updated in synchronism with new data values entered at other workstations.

15. A medical information system as defined in claim 14 further including means for updating the display screen of each of said workstations only when information on said display screen is altered by said database events and only after all database event data has been processed.

16. A medical information system as defined in claim 12 further including means for updating a copy of said record in each of said workstations in response to notification of a database event, including means for obtaining any database event data from a corresponding buffer and means for processing said database event data in sequence so that each of said workstations is updated in synchronism with new data values entered at other workstations.

17. A medical information system as defined in claim 16 further including means for updating the display screen of each of said workstations only when the information on the display screen is altered by said database events and only after all database event data has been processed.

18. A medical information system as defined in claim 10 further including means for displaying said correction history at each of said workstations in response to a request by a user.

* * * * *